(12) United States Patent
Sato et al.

(10) Patent No.: US 8,816,034 B2
(45) Date of Patent: Aug. 26, 2014

(54) METHOD FOR PRODUCING ALPHA-OLEFIN OLIGOMER

(75) Inventors: Hideki Sato, Ichihara (JP); Yushi Matsuda, Ichihara (JP); Jun Kohiruimaki, Ichihara (JP); Masao Aida, Ichihara (JP); Kana Minamimoto, Ichihara (JP); Jun Mase, Ichihara (JP)

(73) Assignee: Idemitsu Kosan Co., Ltd., Tokyo (JP)

( * ) Notice: Subject to any disclaimer, the term of this patent is extended or adjusted under 35 U.S.C. 154(b) by 0 days.

(21) Appl. No.: 13/978,971

(22) PCT Filed: Jan. 11, 2012

(86) PCT No.: PCT/JP2012/000101
§ 371 (c)(1),
(2), (4) Date: Jul. 10, 2013

(87) PCT Pub. No.: WO2012/096160
PCT Pub. Date: Jul. 19, 2012

(65) Prior Publication Data
US 2013/0296518 A1    Nov. 7, 2013

(30) Foreign Application Priority Data

Jan. 14, 2011 (JP) ................. 2011-005501
Jan. 14, 2011 (JP) ................. 2011-005502

(51) Int. Cl.
*C08F 2/38* (2006.01)
*C08F 210/00* (2006.01)
*C08F 10/14* (2006.01)
*C10M 107/10* (2006.01)
*C08F 6/02* (2006.01)
*C07C 2/34* (2006.01)
*C08F 4/659* (2006.01)

(52) U.S. Cl.
CPC ............ *C08F 10/14* (2013.01); *C10N 2270/00* (2013.01); *C10M 107/10* (2013.01); *C08F 4/65912* (2013.01); *C10M 2205/0285* (2013.01); *C10N 2240/10* (2013.01); *C08F 4/65908* (2013.01); *C07C 2531/22* (2013.01); *C08F 6/02* (2013.01); *C07C 2/34* (2013.01)
USPC ............................ 526/348.3; 526/348; 526/82

(58) Field of Classification Search
CPC .. C08F 4/65912; C08F 10/14; C08F 4/65908; C08F 6/02; C10N 2270/00; C10N 2240/10; C10M 107/10; C10M 2205/0285; C07C 2531/22; C07C 2/34
USPC .......................................... 526/82, 348, 348.3
See application file for complete search history.

(56) References Cited

U.S. PATENT DOCUMENTS 6,590,131 B2 * 7/2003 McGinn et al. ............... 585/501

FOREIGN PATENT DOCUMENTS

| JP | 8 301926 | 11/1996 |
| JP | 080301926 | * 11/1996 |

(Continued)

OTHER PUBLICATIONS

International Search Report Issued Apr. 17, 2012 in PCT JP12/00101 Filed Jan. 11, 2012.

(Continued)

*Primary Examiner* — William Cheung
(74) *Attorney, Agent, or Firm* — Oblon, Spivak, McClelland, Maier & Neustadt, L.L.P.

(57) ABSTRACT

A method for producing an α-olefin oligomer including: polymerizing in the presence of a catalyst one or more α-olefins having 6 to 20 carbon atoms to produce an α-olefin oligomer; and deactivating the catalyst by a deactivator from which oxygen is removed. A method for producing an α-olefin oligomer including: polymerizing in the presence of a catalyst one or more α-olefins having 6 to 20 carbon atoms to produce an α-olefin oligomer; and passing the reaction solution containing the α-olefin oligomer through a bag filter.

11 Claims, 5 Drawing Sheets

(56) References Cited

FOREIGN PATENT DOCUMENTS

| | | | |
|---|---|---|---|
| JP | 10-139809 | * | 5/1998 |
| JP | 10 139809 | | 5/1998 |
| JP | 10 158308 | | 6/1998 |
| JP | 2005 162978 | | 6/2005 |
| JP | 2008 231261 | | 10/2008 |
| JP | 2009 7386 | | 1/2009 |
| JP | 2009 504577 | | 2/2009 |

OTHER PUBLICATIONS

U.S. Appl. No. 14/124,933, filed Dec. 9, 2013, Kohiruimaki, et al.
U.S. Appl. No. 14/126,090, filed Dec. 13, 2013, Kohiruimaki, et al.

* cited by examiner

Lower limit of measurement: Al concentration, 0.5 wt ppm, Zr concentration, 0.1 wt ppm

US 8,816,034 B2

METHOD FOR PRODUCING ALPHA-OLEFIN OLIGOMER

This application is the National Stage of International Application PCT/JP2012/000101, filed on Jan. 11, 2012, and claims priority from and the benefit of Japan Patent Application No. 2011-005501, filed on Jan. 14, 2011, and Japan Patent Application No. 2011-005502, filed on Jan. 14, 2011, all of which are incorporated herein by reference in their entireties.

TECHNICAL FIELD

The invention relates to a method for producing an α-olefin oligomer. More particularly, the invention relates to a method for producing an α-olefin oligomer having a smaller amount of catalyst-derived metal components which are mixed in.

BACKGROUND ART

An α-olefin oligomer obtained by polymerizing an α-olefin having 6 to 20 carbon atoms is produced mainly as raw material oil for synthetic lubricant oil such as engine oil. In particular, synthetic lubricant oil composed mainly of an α-olefin oligomer of 1-decene and an α-olefin oligomer of 1-octene and 1-dodecene of such α-olefin oligomers is significantly useful as raw material oil for industrial gear oil and high-performance engine oil. Accordingly, the demand for such synthetic lubricant oil has been increasing.

The above-mentioned α-olefin oligomer can be produced by a method in which monomers are polymerized in the presence of a catalyst, the catalyst is deactivated and the resulting mixture of α-olefin oligomers differing in polymerization degree (trimer, tetramer and pentamer, for example) are fractionated, or by other methods.

The catalyst used for the production of an α-olefin oligomer is normally an organic metal compound. Mixing of metal components contained in a catalyst in an α-olefin oligomer deteriorates the performance of synthetic lubricant oil, and hence, prevention of mixing in of metal components is necessary in order to keep the oil quality.

Patent Document 1 discloses that, for the method for producing an olefin-based polymer in which an organic aluminum compound is used as a catalyst, metal residues of catalyst components can be decreased by adding an oxygen-containing compound having an active proton to a reaction solution after the polymerization and adding water and an alkaline substance such that the pH of an aqueous phase becomes 9 to 13.

Patent Document 2 discloses that an aqueous base phase is mixed with a reaction solution to deactivate a catalyst, the aqueous base phase contains deactivated catalyst components and an organic phase containing an oligomer is separated from the aqueous base phase. Further, Patent Document 2 discloses that, in the method for producing a poly α-olefin, catalyst residues are adsorbed after polymerization by contacting a solid adsorbent, followed by filtration, and alumna, acid clay, Celite or the like are used as the solid adsorbent.

RELATED ART DOCUMENTS

Patent Documents

Patent Document 1: JP-A-2008-231261
Patent Document 2: JP-T-2009-504577

SUMMARY OF THE INVENTION

An object of the invention is to provide a method for producing an α-olefin oligomer which can effectively reduce contamination of metal components derived from a catalyst in an α-olefin oligomer.

According to the invention, the following method for producing an α-olefin oligomer is provided.

1. A method for producing an α-olefin oligomer comprising:
    polymerizing in the presence of a catalyst one or more α-olefins having 6 to 20 carbon atoms to produce an α-olefin oligomer; and deactivating the catalyst by a deactivator from which oxygen is removed.
2. The method for producing an α-olefin oligomer according to 1, wherein the oxygen in the deactivator is removed by nitrogen bubbling.
3. The method for producing an α-olefin oligomer according to 1 or 2, wherein the concentration of oxygen in the deactivator after removal thereof is 1 mg/L or less.
4. The method for producing an α-olefin oligomer according to any of 1 to 3, wherein the catalyst is deactivated in an atmosphere of an inert gas.
5. A method for producing an α-olefin oligomer comprising:
    polymerizing in the presence of a catalyst one or more α-olefins having 6 to 20 carbon atoms to produce an α-olefin oligomer; and passing the reaction solution containing the α-olefin oligomer through a bag filter.
6. The method for producing an α-olefin oligomer according to 5, wherein the filtration rating of the bag filter is 5 μm or less.
7. The method for producing an α-olefin oligomer according to 5 or 6, wherein the filter of the bag filter is formed of polypropylene.
8. An α-olefin oligomer which is produced by the method for producing an α-olefin oligomer according to any of 1 to 7.

According to the invention, a method for producing an α-olefin oligomer which can effectively reduce contamination of catalyst-derived metal components in an α-olefin oligomer can be provided.

MODE FOR CARRYING OUT THE INVENTION

Figure 1:
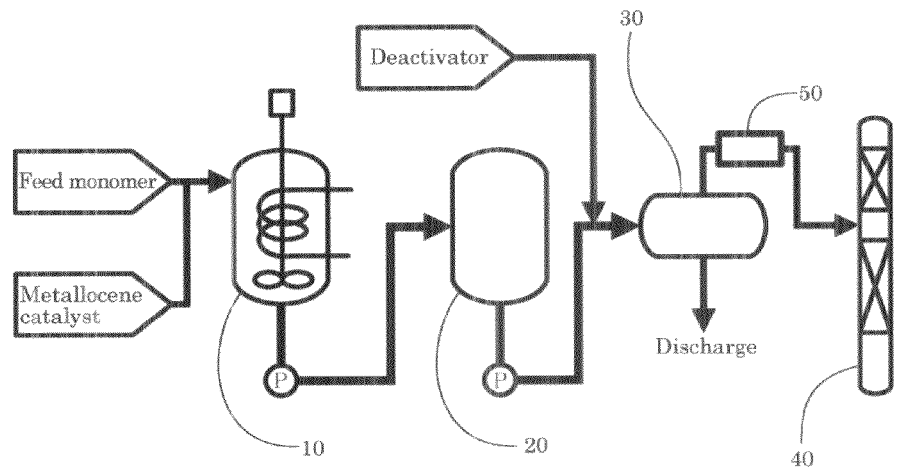
FIG. 1 is a view showing part of one embodiment of the production process of an α-olefin oligomer.

FIG. 1 is a view showing part of one embodiment of the production process of an α-olefin oligomer.

In the production of an α-olefin oligomer, a feed monomer is polymerized in a polymerization vessel 10 by a catalyst (a metallocene catalyst, for example). A mixture of a variety of oligomers (a trimer, a tetramer and a pentamer, for example)

obtained by polymerization is sent to a balance vessel 20, where the process is changed from the batch process to the continuous process. To the oligomer mixture, in a flow path from the balance vessel 20 to a separation vessel 30, an aqueous solution of an alkaline metal hydroxide as a deactivator is added, whereby a catalyst is deactivated. Due to the addition of an aqueous solution of an alkaline metal hydroxide, metal components in the metallocene are precipitated in the form of hydroxides in an aqueous phase (an aqueous solution of an alkaline metal hydroxide), the aqueous phase containing such precipitates and an oil phase containing the oligomer mixture are separated by the separation vessel 30. The aqueous phase containing metal components are discharged in the separation vessel 30, and the oil phase is sent to a distillation columns 40, where oligomers are fractionated.

As mentioned above, it was thought that the catalyst-derived metal components are contained in an aqueous phase and they can be removed by separating in the separation vessel 30.

For example, it was believed that, when an aqueous sodium hydroxide solution is used as a deactivator for the combination of bis(tert-butylcyclopentadienyl)zirconium dichloride as a metallocene catalyst and a MAO (methyaluminoxane) as a co-catalyst, the following reaction proceeds.

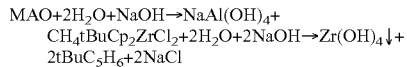

MAO+2H$_2$O+NaOH→NaAl(OH)$_4$+
CH$_4$tBuCp$_2$ZrCl$_2$+2H$_2$O+2NaOH→Zr(OH)$_4$↓+
2tBuC$_5$H$_6$+2NaCl

However, actually, the reaction solution after the deactivation is not clearly separated to an α-olefin oligomer phase (hereinafter, often referred to as the "oil phase") and an aqueous solution phase (hereinafter, often referred to as the "aqueous phase"), and solid sediments are generated at the interface between the oil phase and the aqueous phase. The solid sediments (hereinafter, often referred to as the "precipitates") contain catalyst-derived metal components, and hence, metal components cannot be separated completely only by separating the aqueous phase.

Precipitates which are generated at the interface between the oil phase and the aqueous phase when an aqueous sodium hydroxide solution is used as a deactivator for the combination of bis(tertiary-butylcyclopentadienyl)zirconium dichloride as a metallocene catalyst and MAO (methyaluminoxane) as a co-catalyst is assumed to have the following structure.

Although the compound with the following structure has an organic substance having a cyclopentane framework, since it has an appropriate amount of a hydroxyl group, it can be present at the interface between the oil phase and the aqueous phase as solid sediments.

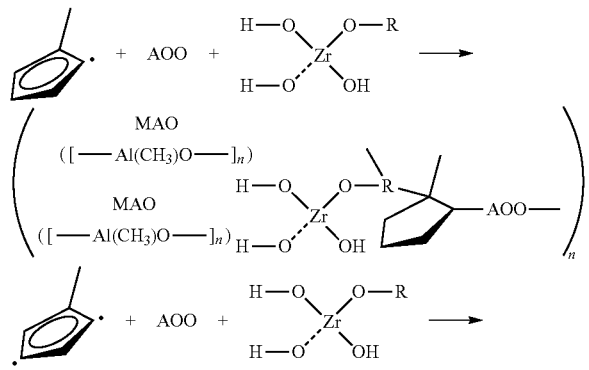

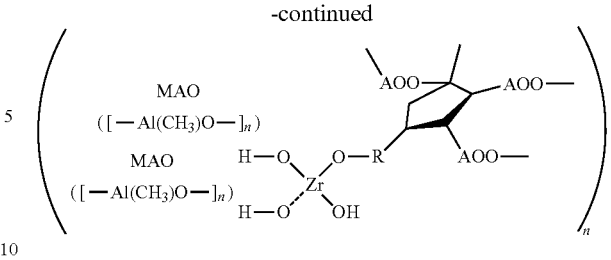

wherein R is an olefin monomer and AOO is an α-olefin oligomer.

In the first method for producing an α-olefin oligomer according to the invention, generation of the above-mentioned precipitates can be significantly reduced by removing oxygen from the deactivator before deactivating a catalyst.

Specifically, in the presence of a catalyst, one or more α-olefins having 6 to 20 carbon atoms are polymerized to produce an α-olefin oligomer, and the oligomer is mixed (liquid-liquid mixing, for example) with a deactivator from which oxygen is removed, thereby to deactivate the catalyst. It is preferred that the mixing be conducted in the atmosphere of an inert gas (nitrogen or the like) (or in the absence of oxygen).

The α-olefin oligomer obtained by the first production method has excellent physical properties as synthetic lubricant oil since almost no catalyst-derived metal components are mixed in. Further, since the formation of precipitates as an impurity can be suppressed, load on a filter or the like during the production process can be decreased, whereby the production cost can be cut.

As a deactivator usable in the first production method, alcohol, water, an acid, an alkali, an oxygen-containing compound and an aqueous solution thereof can be given, for example.

Specific examples of a deactivator include an aqueous sodium hydroxide solution, ethanol, isopropyl alcohol, hydrochloric acid and acetone.

When an organic aluminum compound is used as the catalyst, in respect of the solubility of an aluminum hydroxide compound which is a deactivated product of an organic aluminum compound, a deactivator is preferably an aqueous solution with a pH of 11 to 14, further preferably with a pH of 13 to 14. If an aqueous solution has a pH of less than 11, an aluminum hydroxide compound may be deposited as a solid.

The method for removing oxygen from a deactivator is not particularly restricted as long as it can remove oxygen from a deactivator. However, the removal of oxygen is preferably conducted by inert gas bubbling, further preferably by nitrogen gas bubbling. The inert gas bubbling is conducted for 30 minutes to 48 hours, for example, preferably for 24 to 48 hours.

When the removal of oxygen is conducted by nitrogen bubbling, 1200 L of nitrogen is bubbled into 10 m$^3$ of the deactivator, whereby a deactivator through which nitrogen passed in an amount of 0.12 to 0.24 nitrogen m$^3$/m$^3$ is obtained.

If the amount of nitrogen that passed through a deactivator is less than 0.12 m$^3$/m$^3$, oxygen may not be removed completely. On the other hand, if the amount of nitrogen that passed through a catalyst exceeds 0.24 nitrogen m$^3$/m$^3$, deactivator components may be evaporated.

As means for removing oxygen from a deactivator, in addition to the above-mentioned bubbling with inert gas, methods such as a gas-liquid contact method including a stripping method and a method using an oxygen remover can be given.

Removal of oxygen with the above-mentioned oxygen remover can be conducted by a method in which an oxygen remover is added to a deactivator such that the concentration of an oxygen remover in the deactivator becomes around several thousands ppm. As the oxygen remover, hydrosulfate or the like can be given.

In the first production method, there are no particular restrictions as long as a deactivation reaction can be conducted in a state in which the amount of oxygen in a reaction solution is kept small. For example, if the pH of the deactivator in the form of an aqueous solution is adjusted, oxygen can be removed from an aqueous solution and water before adjustment, or oxygen may be removed after adjustment of pH.

The deactivator from which oxygen is removed preferably has an oxygen concentration of 1 mg/L or less, more preferably 0.1 mg/L or less. It is further preferred that the deactivator contain substantially no oxygen (less than the lower limit of measurement).

The above-mentioned "oxygen concentration" indicates the concentration of dissolved oxygen in the deactivator. The oxygen concentration can be measured by means of a galvanic cell type oxygen meter (DO-24P, a portable dissolved oxygen meter manufactured by DKK-TOA Corporation).

In the second method for producing an α-olefin oligomer of the invention, in the presence of a catalyst, an α-olefin oligomer is produced by polymerizing one or more α-olefin oligomers having 6 to 20 carbon atoms to produce an α-olefin oligomer, and a reaction solution containing the α-olefin oligomer is passed through a bag filter.

In the second production method, by passing a reaction solution containing an α-olefin oligomer after the deactivation reaction through a bag filter, catalyst-derived metal components can be removed, whereby physical properties of the resulting α-olefin oligomer can be improved. Further, since the bag filter has a longer life as compared with that of a sintered metal filter since it hardly causes clogging, it can contribute to cut the production cost.

In the second production method, in the process shown in FIG. 1, a bag filter 50 is provided from a separation vessel 30 to a distillation columns 40. By passing an oil phase which is separated by the separation vessel 30 through the bag filter 50, catalyst-derived metal components are removed.

The bag filter 50 may be provided at any position between the distillation tower 40 and a product tank. However, it is preferred that the bag filter 50 be provided between the separation vessel 30 and the distillation columns 40 since the viscosity of the solution is low due to the large amount of unreacted raw materials or light components therebetween.

It is preferred that the bag filter have a nominal filtration rating, which may be referred to as "filtration rating" hereinafter, of 5 μm or less, more preferably 3 μm or less, and particularly preferably 1 μm or less. Further, the bag filter preferably has an absolute filtration rating of 15 μm or less, more preferably 10 μm and particularly preferably 5 μm or less. If the filtration rating is too large, precipitates cannot be captured sufficiently.

As for the nominal filtration rating and the absolute filtration rating, the "absolute filtration rating" means that 99.9% or more of particles with an indicated diameter are captured, and the "nominal filtration rating" means that 80% or more of particles with an indicated diameter are captured.

The material of the filter of the bag filter used is not particularly restricted, and a filter formed of nylon, polypropylene or the like may be used, for example. A filter formed of polypropylene is preferable.

In general, in respect of life or required power, it is preferred that a filter be used at a low pressure drop. If pressure drop is high, a treatment may not be conducted unless the filtration area is increased. If the filter of the bag filter is formed of polypropylene, in respect of the filter structure, a high filtration rating can be obtained with a low pressure drop. Accordingly, the power such as a pump can be decreased.

An α-olefin having 6 to 20 carbon atoms used in the first and second methods for producing an α-olefin oligomer (hereinafter referred to as the "method for producing an α-olefin oligomer of the invention") is preferably an α-olefin having 6 to 14 carbon atoms, more preferably an α-olefin having 8 to 12 carbon atoms, and further preferably 1-decene, 1-octene and 1-dodecene.

As the catalyst used in the method for producing an α-olefin oligomer of the invention, a metallocene catalyst such as (1,1'-dimethylsilylene)(2,2'-dimethylsilylene)-bis(cyclopentadienyl)zirconium dichloride and a compound shown by the following formula (I) can be used.

$$(RC_5H_4)_2MX_2 \qquad (I)$$

wherein R is a hydrogen atom or a hydrocarbon group having 1 to 10 carbon atoms;

M is a transitional metal element belonging to the fourth group of the periodic table of elements; and X is a covalent ligand or an ionic ligand.

In the formula (I), R is preferably a hydrogen atom or a hydrocarbon group having 1 to 4 carbon atoms.

Specific examples of M include titanium, zirconium and hafnium. Of these, zirconium is preferable.

Specific example of X include a hydrogen atom, a halogen atom, a hydrocarbon group having 1 to 20 (preferably 1 to 10) carbon atoms, an alkoxy group having 1 to 20 (preferably 1 to 10) carbon atoms, an amino group, a phosphorous-containing hydrocarbon group having 1 to 20 (preferably 1 to 12) carbon atoms (a diphenylphosphine group, for example), a silicon-containing hydrocarbon group having 1 to 20 (preferably 1 to 12) carbon atoms (a trimethylsilyl group, for example), a boron compound containing a hydrocarbon group having 1 to 20 (preferably 1 to 12) carbon atoms, or halogen (for example, $B(C_6H_5)_4$, $BF_4$) can be given. Of these, a hydrogen atom, a halogen atom, and a group selected from a hydrocarbon group and an alkoxy group are preferable.

Specific examples of the metallocene compound represented by the above formula (I) include bis(cyclopentadienyl)zirconium dichloride, bis(methylcyclopentadienyl)zirconium didichloride, bis(ethylcyclopentadienyl)zirconium dichloride, bis(iso-propylcyclopentadienyl)zirconium dichloride, bis(n-propylcyclopentadienyl)zirconium dichloride, bis(n-butylcyclopentadienyl)zirconium dichloride, bis(t-butylcyclopentadienyl)zirconium dichloride, bis(thexylcyclopentadienyl)zirconium dichloride, bis(trimethylsilylcyclopentadienyl)zirconium dichloride, bis(trimethylsilylmetylcyclopentadienyl)zirconium dichloride, bis(cyclopentadienyl)zirconium chlorohydride, bis(cyclopentadienyl)methylzirconium chloride, bis(cyclopentadienyl)ethylzirconium chloride, bis(cylopentadienyl)methoxyzirconium chloride, bis(cyclopentadieny)phenylzirconium chloride, bis(cyclopentadienyl)dimethylzirconium, bis(cyclopentadienyl)diphenylzirconium, bis(cyclopentadienyl)dineopentylzirconium, bis(cyclopentadienyl)dihydrozirconium, and bis(cyclopentadienyl)dimethoxyzirconium. Of these, bis(t-butylcyclopentadienyl)zirconium dichloride can be preferably given.

Further, those obtained by replacing a chlorine atom of these compounds by a bromine atom, an iodine atom, a hydrogen atom, a methyl group, a phenyl group or the like, or those obtained by replacing zirconium as the central metal of these compounds by titanium and hafnium can be given.

Methylaluminoxane can be used in combination with the above-mentioned metallocene catalyst.

As the above-mentioned methylaluminoxane, known methylaluminoxanes can be used. For example, a chain or cyclic methylaluminoxane represented by the following formula (II) or (Ill) can be given.

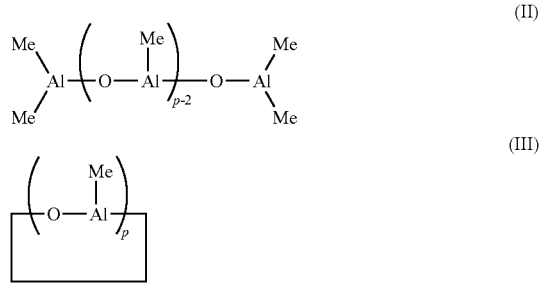

In the formulas (II) and (III), p is a polymerization degree which is normally 3 to 50, preferably 7 to 40. The methylaluminoxane may be used alone or in combination of two or more.

As for the amount ratio of the metallocene compound and the methylaluminoxane, the molar ratio of methylaluminoxane/metallocene compound is normally 15 to 150, preferably 20 to 120, and further preferably 25 to 100. If the molar ratio is less than 15, the catalytic activity may not be developed. In addition, a dimer of an α-olefin tends to be generated easily, and as a result, a yield of an oligomer larger than a trimer may be decreased. On the other hand, if the molar ratio exceeds 150, removal of the catalyst-derived metal component may be insufficient.

In respect of productivity, the production method of the invention is preferably carried out without using a solvent. It is possible to use a solvent. In this case, an aromatic hydrocarbon such as benzene, toluene, xylene and ethylbenzene; an alicyclic hydrocarbon such as cyclopentane, cyclohexane and methylcyclohexane; an aliphatic hydrocarbon such as pentane, hexane, heptane and octane and halogenated hydrocarbon such as chloroform and dichloromethane can be used. These solvents may be used singly or in combination of two or more. Further, a monomer such as 1-butene can be used as a solvent.

In the production method of the invention, there are no particular restrictions being imposed on the polymerization method. Any of bulk polymerization, solution polymerization, suspension polymerization, slurry polymerization, and vapor phase polymerization may be used.

As for the polymerization conditions, the polymerization temperature is normally 0 to 200° C., preferably 30 to 150° C. and more preferably 40 to 120° C. As for the amount ratio of the catalyst relative to the raw monomer, it is preferred that the raw monomer/the metallocene catalyst (molar ratio) be 1 to $10^8$, particularly 100 to $10^5$. Further, the polymerization time is normally 5 minutes to 20 hours, and the reaction pressure is preferably from normal pressure to 0.2 MPaG, with from normal pressure to 0.1 MPaG being particularly preferable.

In the invention, a preliminary polymerization can be conducted by using the above-mentioned catalyst for polymerization.

A preliminary polymerization can be conducted by allowing a small amount of olefin to contact catalyst components, for example. No specific restrictions are imposed on the method, and a known method can be used. No specific restrictions are imposed on the olefin used in a preliminary polymerization, and ethylene, an α-olefin having 3 to 20 carbon atoms or a mixture thereof can be used. It is advantageous to use the same olefin as the monomer used in this polymerization.

A preliminary polymerization temperature is normally −20° C. to 200° C., preferably −10° C. to 130° C., and more preferably 0° C. to 80° C.

In a preliminary polymerization, as a solvent, an inert hydrocarbon, an aliphatic hydrocarbon, an aromatic hydrocarbon, a monomer or the like can be used. Of these, an aliphatic hydrocarbon and an aromatic hydrocarbon are particularly preferable.

Further, a preliminary polymerization may be conducted without using a solvent. In a preliminary polymerization, it is preferred that conditions be adjusted such that the amount of a preliminary polymerization product relative to one mmol of transitional metal components in catalyst is preferably 1 to 10,000 g, in particular 1 to 1,000 g.

EXAMPLES

The invention will be explained hereinbelow with reference to the following examples which should not be construed as limiting the scope of the invention.

Example 1

A stainless-made autoclave with an inner volume of 1 liter was completely dried, and replaced with nitrogen. Then, 200 mL of 1-decene was placed, and the temperature thereof was elevated to 40° C. After adding 0.5 mmol of methylaluminoxane (0.25 ml of a toluene solution of 2.0 mmol/ml), 5 μmol of bis(t-butylcyclopentadienyl)zirconium dichloride (1 ml of a toluene solution of 5 μmol/ml) were placed. Immediately after, hydrogen was introduced to allow the reaction pressure to be 0.05 MPaG, and polymerization was started. After 120 minutes from the start of the polymerization, the temperature was lowered to room temperature, and a polymerization solution containing a decene oligomer was transferred to a nitrogen-filled bottle with a Schlenk cork in the atmosphere of nitrogen.

Figure 2:
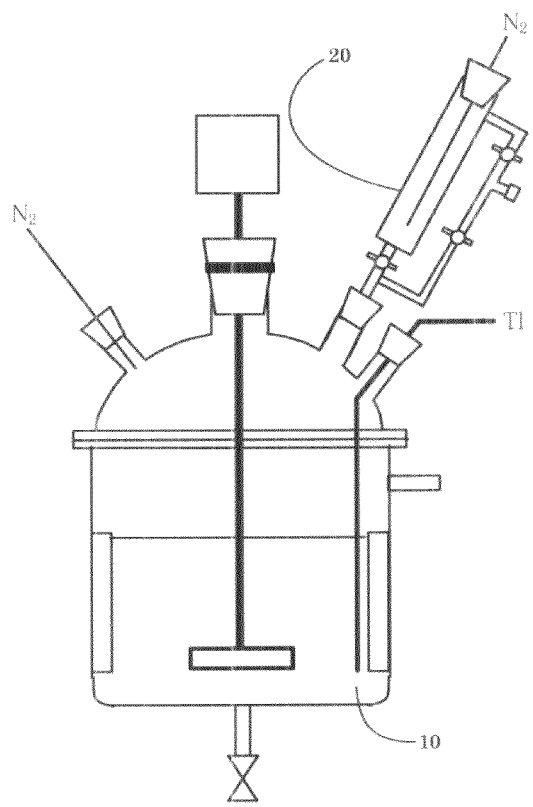
FIG. 2 is a schematic view of an apparatus used for deactivation of a catalyst.

Deactivation of a catalyst contained in the polymerization solution was conducted by means of an apparatus shown in FIG. 2.

An agitation vessel 10 of FIG. 2 was purged with nitrogen. With a syringe, 400 mL of a polymerization solution in the bottle with a Schlenk cork was placed in an agitation vessel, and the solution was heated to 50° C. with stirring. 100 mL of an aqueous NaOH solution (pH 13) treated by having nitrogen bubbled through for 44 hours was placed in an input tube 20. The concentration of dissolved oxygen in an aqueous NaOH solution after nitrogen bubbling with a galvanic cell type oxygen meter (DO-24P, a portable dissolved oxygen meter manufactured by DKK-TOA Corporation) was found to be 4 wt ppm.

An aqueous NaOH solution after nitrogen bubbling was input to the agitation vessel 10, and the catalyst was deactivated with stirring for 10 minutes. Stirring was stopped and the solution was allowed to stand for 30 minutes. The solution was separated into an oil phase and an aqueous phase, and precipitates at the interface of the oil phase and the aqueous phase could not be confirmed by observing the inside of the vessel.

The resulting oil phase was filtered with a filter having a pore size of 1.00 μm (T100A-, manufactured by Advantech Co., Ltd.), and the resulting residues were washed with toluene to measure the weight of precipitates (constant weights of residues and filter paper after drying—constant weight of filter paper before filtration). As a result, the weight of precipitates which were captured was 0.0091 g, and the concentration of precipitates in the oil phase was 15 wt ppm.

Comparative Example 1

A decene oligomer was produced in the same manner as in Example 1, except that no nitrogen bubbling was conducted for an aqueous NaOH solution of the deactivator, and the atmosphere of the agitation vessel was air without replacing the atmosphere inside the vessel by nitrogen. The resulting precipitates were evaluated. As a result, it was found that the amount of the precipitates which were captured was 0.2185 g relative to 156 g of the oil phase.

White solid sediments (precipitates) were generated between the oil phase and the aqueous phase by observing the inside of the agitation vessel. That is, essentially three phases were confirmed.

Reference Example 1

The agitation vessel 10 shown in FIG. 2 was purged by a certain amount of nitrogen. A simulated solution was placed in the agitation vessel 10, and the solution was heated to 50° C. with stirring. Into the input tube 20, 100 mL of an aqueous NaOH solution (pH 13) was placed, followed by nitrogen bubbling for 44 hours. The concentration of dissolved oxygen in the aqueous NaOH solution after nitrogen bubbling with a galvanic cell type oxygen meter (DO-24P, a portable dissolved oxygen meter manufactured by DKK-TOA Corporation), and was found to be 4 wt ppm.

The aqueous NaOH solution after nitrogen bubbling was put to the agitation vessel 10. Deactivation of a catalyst was conducted by stirring for 10 minutes. The stirring was stopped and the solution was allowed to stand for 30 minutes.

The concentration of a monomer oxide generated in the resulting oil phase was evaluated. The monomer oxide concentration reflects the amount of oxygen in the agitation vessel which could not be removed by nitrogen purge. The concentration of the precipitates in the oil phase was evaluated. The results are shown in Table 1.

The simulated solution mentioned above was obtained by putting a catalyst in the polymerization solution after washing with water.

Reference Examples 2 to 7

Figure 3:
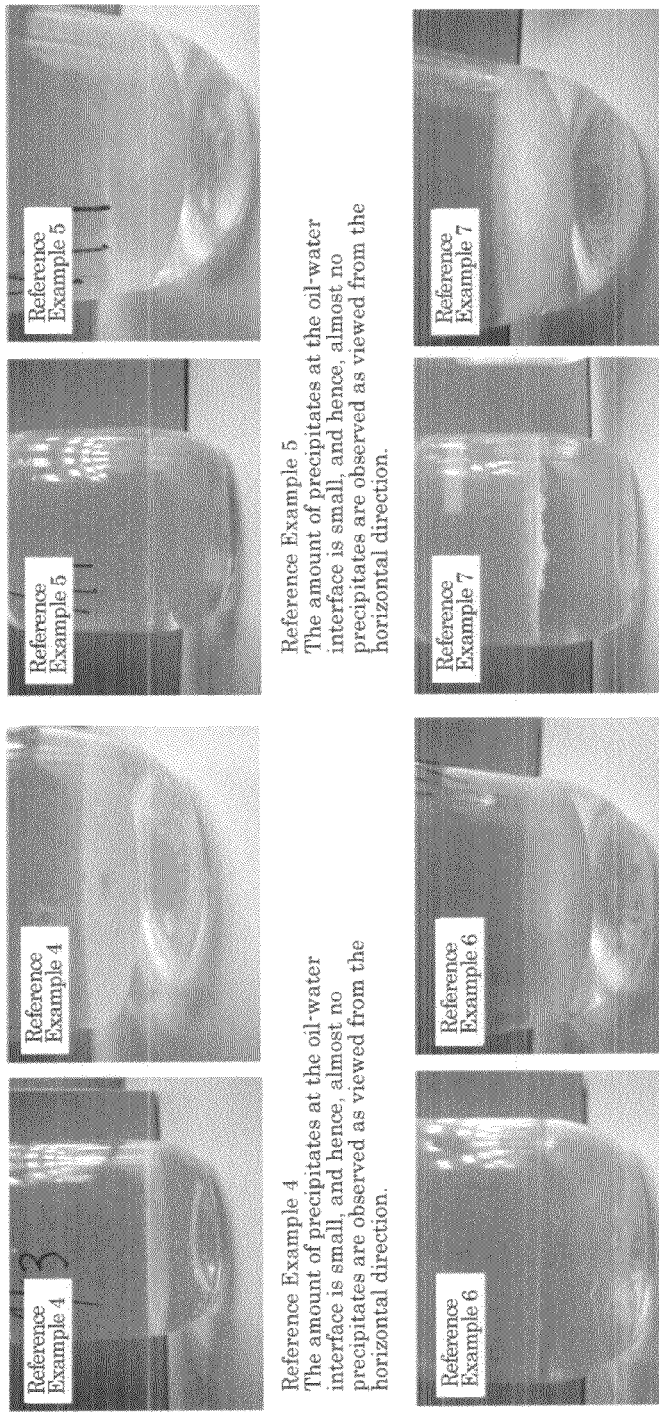
FIG. 3 is a view showing the oil phases, the precipitates and the aqueous phases of Reference Examples 4 to 7.

In Reference Examples 2 to 6, the concentration of the monomer oxide generated in the oil phase and the concentration of the precipitates were evaluated in the same manner as in Reference Example 1. Reference Example 7 is the same as Comparative Example 1. The results are shown in Table 1. As for Reference Examples 4 to 7, the three phases, i.e. the oil phase, the precipitates and the aqueous phase, were photographed. The results are shown in FIG. 3.

TABLE 1

| | Concentration of oxides [wtppm] | Amount of generated precipitates [g] | Concentration of precipitates [wtppm] |
|---|---|---|---|
| Ref. Ex. 1 | 11 | — | — |
| Ref. Ex. 2 | 6 | — | — |
| Ref. Ex. 3 | 8 | 0.0193 | 104 |
| Ref. Ex. 4 | 3 | 0.0062 | 33 |
| Ref. Ex. 5 | — | 0.0053 | 28 |
| Ref. Ex. 6 | 5.4 | 0.0145 | 78 |
| Ref. Ex. 7 | — | 0.2185 | 140 |

Figure 4:
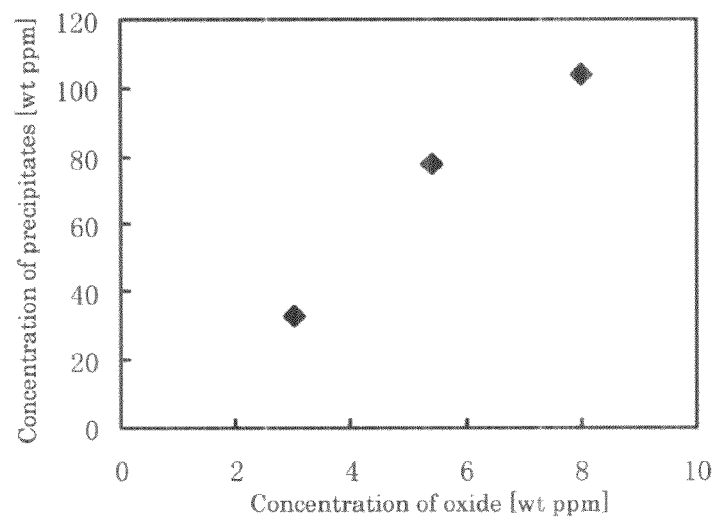
FIG. 4 is a view showing the relationship between the oxide concentration and the concentration of precipitates.

For Reference Examples 3, 4 and 6, the relationship between the oxygen concentration and the concentration of the precipitates is shown in FIG. 4, taking the abscissa and the vertical axis as the oxide concentration and the precipitate concentration, respectively. Table 1 and FIG. 4 demonstrate that the concentration of the precipitates was increased with an increase in the concentration of an oxide (a decrease in the amount of nitrogen purge flow). This indicates that the oxygen amount relates to generation of the precipitates.

Evaluation Example 1

A stainless-made autoclave with an internal volume of 1 liter was completely dried, and replaced with nitrogen. Then, 200 ml of 1-decene and 0.8 mmol of methylaluminoxane were placed, and the temperature was increased to 40° C. After inputting 8 micromoles of bis(t-butylcyclopentadienyl) zirconium dichloride, 2 KPaG of hydrogen was introduced to start polymerization. After conducting a reaction at 40° C. for 5 hours, the resultant was added to 50 mL of a 1 wt % aqueous NaOH solution, followed by stirring.

Figure 5:
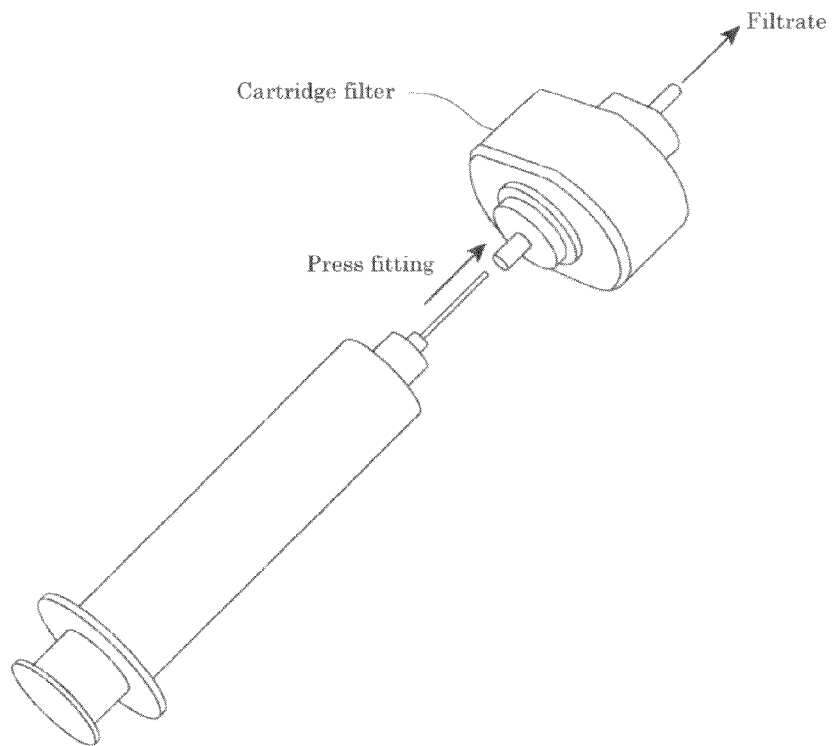
FIG. 5 is a view showing the evaluation method of Evaluation Example 1.

For the filtration of the resulting oil phase (organic phase), a depth-pleated type cartridge filter (SHP-020-M25DKC, manufactured by Roki Techno Co., Ltd., Filtration area: 4.9 cm$^2$) having a filtration rating of 2 μm was used to evaluate the filtration time. Specifically, as shown in FIG. 5, 60 ml of the oil phase was collected by using a 200-mL syringe while the oil phase was mixed with stirring, and the syringe was then connected to a filtration apparatus provided with the above-mentioned cartridge filter and the corrected oil phase was pushed under pressure to pass through the filter. The time from the start to the completion of passage in was taken as the filtration time. As a result, the filtration time was found to be 210 seconds.

The filtrate after the filtration was separated by allowing it to stand. The thus separated polymer solution was subjected to ashing by adding sulfuric acid. The aluminum concentration was measured by alkali fusion AAS, and the concentration of aluminum was 2 wt ppm. By the visual observation, the resulting filtrate was a turbid solution. The results are shown in Table 2.

Evaluation Examples 2 to 5

Filtration was conducted in the same manner as in Evaluation Example 1 by using the filters shown in Table 2 for the periods of time shown in Table 2, and the metal concentration in the filtrate and the resulting filtrate were visually observed. The results are shown in Table 2.

The cartridge filters in Evaluation Examples 2 to 4 were SHP-030-M25DKC, SHP-050-M25DKC and SNP-030-M25DKC, respectively. No cartridge filter was used in Evaluation Example 5.

TABLE 2

| | Filter for treatment | | | Al concentration [wt ppm] | Filtration time | Filtrate |
|---|---|---|---|---|---|---|
| | Filtration rating | Type | Material | | | |
| Evaluation Ex. 1 | 2 μm | Depth-pleated | Polypropylene | 2 | 210 sec | Turbid |
| Evaluation Ex. 2 | 3 μm | Depth-pleated | Polypropylene | 5 | 140 sec | Turbid |
| Evaluation Ex. 3 | 5 μm | Depth-pleated | Polypropylene | 7 | 90 sec | Turbid |
| Evaluation Ex. 4 | 3 μm | Depth-pleated | All nylon | <<1 | 30 minutes or more | Transparent |
| Evaluation Ex. 5 | — | | | 32 | — | Turbid |

Example 2

Figure 6:
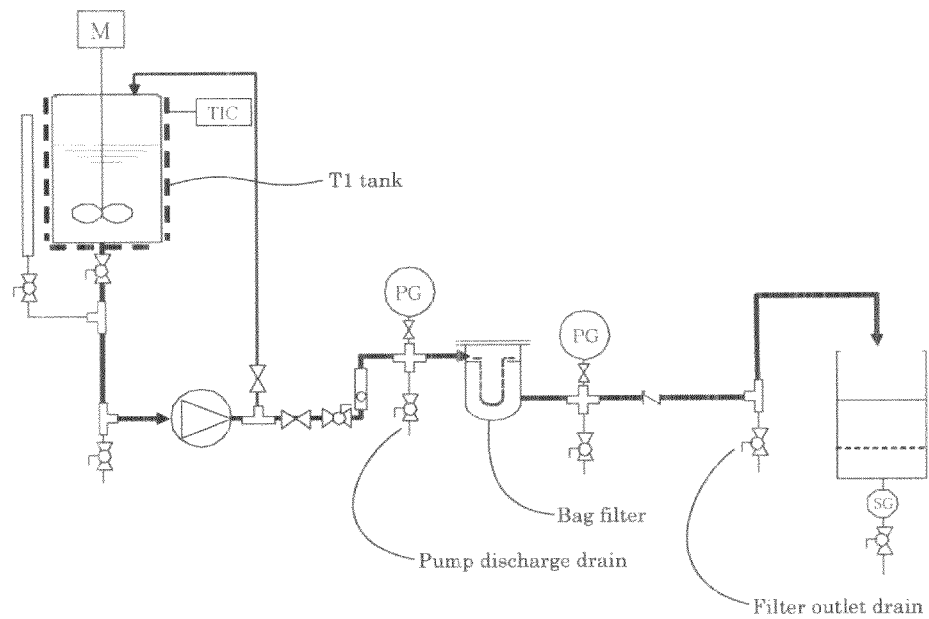
FIG. 6 is a view showing the process in Example 2.

The bag filter was evaluated by using the apparatus shown in FIG. 6.

16 L of an α-olefin oligomer solution obtained in the same manner as in Evaluation Example 1 was placed in a tank (T1). The solution was heated to 60° C. with stirring by means of a tape heater. When the solution reached the prescribed temperature, 4 L of a 1 wt % aqueous NaOH solution which had been diluted with pure water was added, and stirring was continued for 15 minutes. Further, the resultant was allowed to stand for 15 minutes, whereby the resultant was separated into an oil phase and an aqueous phase. Thereafter, from the bottom of a T1 tank, an aqueous NaOH solution was taken out. When the mixture of precipitates into the solution was visually confirmed, taking out of an aqueous phase was stopped.

The remaining oil phase was stirred again to allow the precipitates to be dispersed. Thereafter, the pump was started, and the oil was passed through a bag filter (AccuGAF filter bag AGF-53 manufactured by Eaton Corporation, formed of polypropylene) at a constant flow rate of 4 L/min to confirm the pressure before and after the filter.

Figure 7:
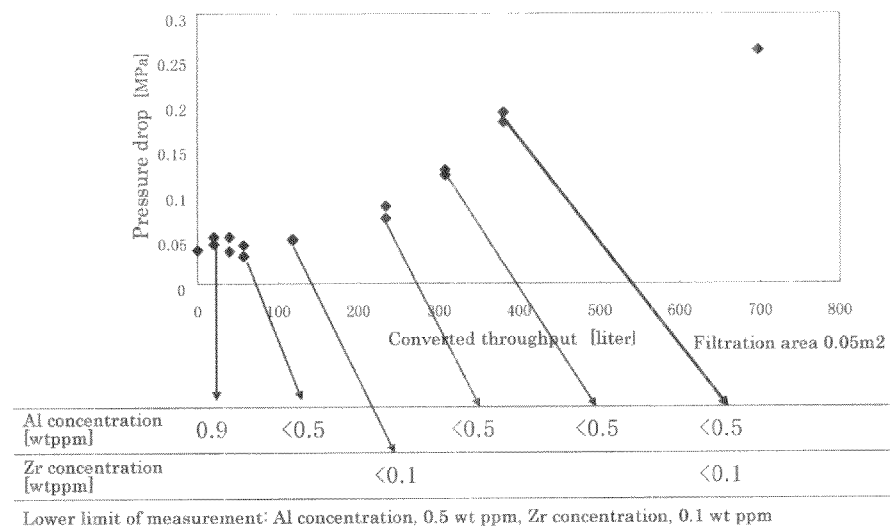
FIG. 7 is a view showing the filtration rating of Example 2.

During the passage of the oil phase, sampling was conducted from the pump discharge drain and the filter outlet drain. The concentration of precipitates was quantified from the filter inlet sample and the concentrations of Al and Zr in the oil phase from the filter outlet sample to confirm the filtration rating. The results are shown in FIG. 7.

The Al concentration was evaluated by alkali fusion AAS after adding sulfuric acid and ashing. The Zr concentration was evaluated by ICP-AES method after ashing and an acid treatment.

Example 3

Figure 8:
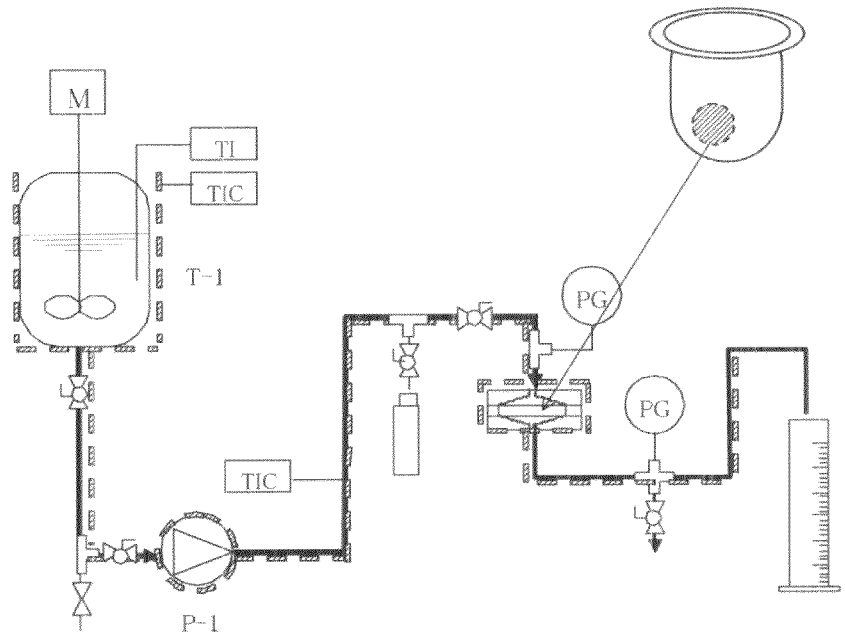
FIG. 8 is a view showing the process in Example 3.

By using an apparatus shown in FIG. 8, the bag filter used in Example 2 was cut such that the filtration area became 0.00062 m². The oil phases which were obtained by the method described below were passed through the filter at a flow rate of 50 ml/min. The following three polymerization solutions were passed through. Specifically, a polymerization solution (30 L-20° C. alkaline washed oil phase) obtained by using a 30 L-reactor and putting 1 wt % aqueous NaOH solution to a polymerization solution at 20° C. for stopping the polymerization; a polymerization solution (30 L-80° C. alkaline washed oil phase) obtained by using a 30 L-reactor and putting 1 wt % aqueous NaOH solution to a polymerization solution at 80° C. for stopping the polymerization; and a polymerization solution (100 L-80° C. alkaline washed oil phase) obtained by using a 100 L-reactor and putting 1 wt % aqueous NaOH solution to a polymerization solution at 80° C. for stopping the polymerization.

Figure 9:
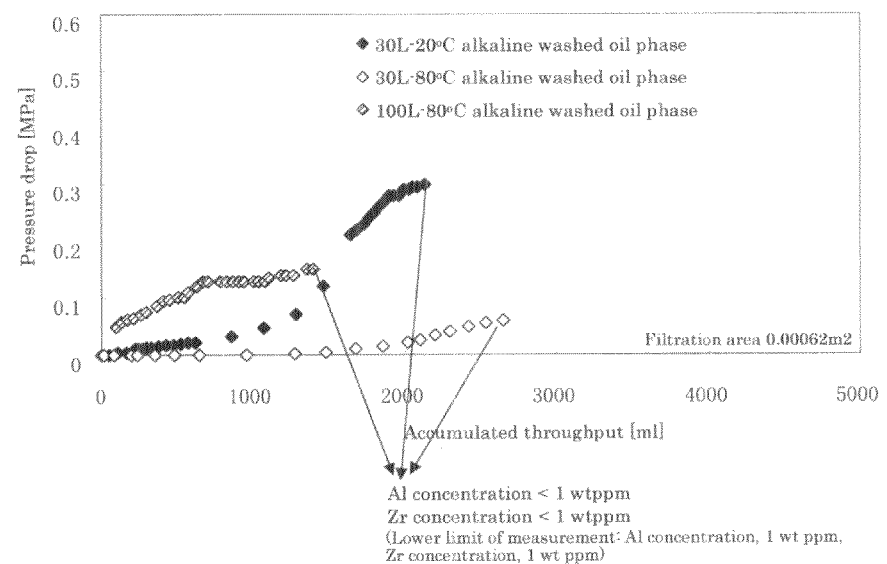
FIG. 9 is a view showing the filtration rating of Example 3.

During the passage of the oil phase, sampling was conducted from the pump discharge drain and the filter outlet drain, the concentration of precipitates was quantified by the inlet sample. In the same manner as in Example 2, the concentrations of Al and Zr in the oil phase after the passage from the outlet sample were respectively evaluated to confirm the filtration rating. The results are shown in FIG. 9.

The oil phases evaluated as above were obtained by enlarging the scale of the following method according to the size of the reactor.

A stainless-made autoclave with an inner volume of 5 L was completely dried. After replacement by nitrogen, 1750 ml of 1-dodecene, 1250 ml of 1-octene and subsequently 1.5 mmol of triisobutyl aluminum were placed therein. The temperature was elevated to 105° C. After putting 24 ml of a catalyst mixture solution, 0.05 MPaG of hydrogen was introduced to start the polymerization. After the lapse of 120 minutes, 24 ml of the remaining catalyst mixture was added, and the resultant was allowed to react at 105° C. for 120 minutes. The content was taken out and added to 750 ml of a 1 wt % aqueous NaOH solution. The resulting mixture was stirred and the polymerization was stopped. This solution was transferred to a separatory funnel to isolate the oil phase.

The above-mentioned catalyst mixture solution was obtained as follows. Specifically, in a 100 mL-glass made bottle with a Schlenk cork, 3 mmol of triisobutyl aluminum (6 mL of a toluene solution of 0.5 mmol/mL), 60 μmol of (1,1'-dimethylsilylene)(2,2'-dimethylsilylene)-bis(cyclopentadienyl)zirconium dichloride (12 mL of a toluene solution of 5 μmol/mL) and 0.12 mmol (96 mg) of powdery N,N-diemthylanilinium tetrakis(pentafluorophenyl)borate were placed, and the resultant was stirred at room temperature for 1 minute. Thereafter, 15 mL of 1-octene and 15 mL of 1-dodecene were added, followed by further stirring for 1 hour at room temperature.

INDUSTRIAL APPLICABILITY

The α-olefin oligomer obtained by the method of the invention can be preferably used for lubricant oil which requires high quality since it contains almost no catalyst-derived metal components.

Although only some exemplary embodiments and/or examples of this invention have been described in detail above, those skilled in the art will readily appreciate that many modifications are possible in the exemplary embodiments and/or examples without materially departing from the novel teachings and advantages of this invention. Accordingly, all such modifications are intended to be included within the scope of this invention.

The documents described in the specification are incorporated herein by reference in its entirety.

The invention claimed is:

1. A method for producing an α-olefin oligomer, the method comprising:
   polymerizing in the presence of a catalyst one or more α-olefins having 6 to 20 carbon atoms to produce an α-olefin oligomer; and
   deactivating the catalyst by a deactivator from which oxygen is removed, wherein a concentration of oxygen in the deactivator after removal thereof is 1 mg/L or less.

2. The method for producing an α-olefin oligomer according to claim 1, wherein the oxygen in the deactivator is removed by nitrogen bubbling.

3. The method for producing an α-olefin oligomer according to claim 1, wherein the catalyst is deactivated in an atmosphere of an inert gas.

4. A method for producing an α-olefin oligomer, the method comprising:
   polymerizing in the presence of a catalyst one or more α-olefins having 6 to 20 carbon atoms to produce an α-olefin oligomer; and
   passing the reaction solution containing the α-olefin oligomer through a bag filter, wherein a filtration rating of the bag filter is 5 μM or less.

5. The method for producing an α-olefin oligomer according to claim 4, wherein a filter of the bag filter comprises polypropylene.

6. An α-olefin oligomer which is produced by the method for producing an α-olefin oligomer according to claim 1, wherein the α-olefin oligomer comprises 15 wt ppm or less of precipitate.

7. The method for producing an α-olefin oligomer according to claim 2, wherein the catalyst is deactivated in an atmosphere of an inert gas.

8. An α-olefin oligomer which is produced by the method for producing an α-olefin oligomer according to claim 2, wherein the α-olefin oligomer comprises 15 wt ppm or less of precipitate.

9. An α-olefin oligomer which is produced by the method for producing an α-olefin oligomer according to claim 3, wherein the α-olefin oligomer comprises 15 wt ppm or less of precipitate.

10. An α-olefin oligomer which is produced by the method for producing an α-olefin oligomer according to claim 4, wherein the α-olefin oligomer comprises 15 wt ppm or less of precipitate.

11. An α-olefin oligomer which is produced by the method for producing an α-olefin oligomer according to claim 5, wherein the α-olefin oligomer comprises 15 wt ppm or less of precipitate.

* * * * *